(12) United States Patent
Hersh

(10) Patent No.: US 6,630,442 B1
(45) Date of Patent: *Oct. 7, 2003

(54) REPARATIVES FOR CHEMOSURGERY AND LASER (THERMAL) THERAPY

(76) Inventor: Theodore Hersh, 3201 Andrews Ct. NW., Atlanta, GA (US) 30305

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 991 days.

(21) Appl. No.: 08/781,868

(22) Filed: Jan. 10, 1997

(51) Int. Cl.$^7$ .................. A01N 37/18; A61K 38/00; A61K 9/00
(52) U.S. Cl. .................. 514/2; 514/110; 514/547; 514/844; 514/886; 424/401; 424/59; 424/63; 424/520
(58) Field of Search .................. 514/2, 110, 547, 514/844, 886; 424/59, 63, 520, 401

(56) References Cited

U.S. PATENT DOCUMENTS

| | | | | |
|---|---|---|---|---|
| 4,865,840 A | * | 9/1989 | Burke et al. | 424/59 |
| 4,942,031 A | * | 7/1990 | Levin | 424/520 |
| 5,128,365 A | * | 7/1992 | Spector | 514/422 |
| 5,330,757 A | * | 7/1994 | Burke | 424/449 |
| 5,384,116 A | * | 1/1995 | Pawalek et al. | 424/63 |
| 5,427,778 A | * | 6/1995 | Finkenauer | 424/78.08 |
| 5,516,507 A | * | 5/1996 | N'guyen | 424/59 |
| 5,565,439 A | * | 10/1996 | Piazza et al. | 514/110 |
| 5,582,817 A | * | 12/1996 | Otsu | 424/59 |
| 5,618,521 A | * | 4/1997 | De Rigal | 424/59 |
| 5,627,212 A | * | 5/1997 | Cavazza | 514/547 |

* cited by examiner

*Primary Examiner*—Mary K. Zeman

(57) ABSTRACT

A composition of glutathione and selenium, as a selenoamino acid or selenium yeast extract and an epidermal growth factor in a topical carrier and method of using the composition to reduce and repair skin damage, resulting from aesthetic (exfoliation and chemical peels) and surgical (laser and other therapies) procedures and other chemical and thermal burns to the cutaneous tissues.

10 Claims, No Drawings

REPARATIVES FOR CHEMOSURGERY AND LASER (THERMAL) THERAPY

TECHNICAL FIELD OF THE INVENTION

The present invention deals with the combination of several anti-oxidants, including enzymatic co-factors and thiol compounds, and various tissue and cell growth stimulating factors in appropriate delivery vehicles employed in topical carriers as a means of ameliorating complications and also concomitantly enhancing repair from free radical damage to the skin undergoing treatment with exfoliants or chemosurgery (chemical peels) and laser (thermal injury) therapy and also stimulating the growth, differentiation and maturation of epidermal cells resulting both from these aesthetic therapeutic procedures or interventions, burns and the existing complicating environmental and cellular metabolic factors, which also engender abundant free radicals in cutaneous tissues.

BACKGROUND OF THE INVENTION

When cutaneous tissues are exposed to radiation, such as solar ultraviolet rays (UVA and UVB radiation), burns from chemical and thermal injuries, damage to the skin ensues, particularly exposure to UVB which results in sunburn and tanning., Many common pathologic factors exist as the various layers of skin are injured from local release of free radical species, emanating from cellular metabolism and enhanced by the putative inflammatory injury.

Skin peeling programs (chemical or thermal peels) are designed to remove "dead" skin with the aim of being replaced by new, clearer and younger cells yielding smooth and firmer skin. These treatments are recommended for solar (ultraviolet radiation) damaged skin, scarring resulting from skin conditions such as acne or for embarrassing cutaneous large pores, fine lines or the so-called "razor bumps." Home treatments (exfoliation with enzymes or alpha hydroxy acids) have been designed to bring about the separation and removal of dead skin, particularly from the face and neck without causing bleeding or scabbing or breakage of deeper dermal tissues. To avoid uneven skin results, these exfoliating chemical treatments need be applied evenly, unlike the uneven solar damage to the skin. These home peel treatments need be repeated periodically; however, for severe skin conditions or problems, stronger chemical treatments or more prolonged applications or laser therapy need be performed by aesthetic professionals or medical practitioners of the art, such as plastic surgeons or dermatologists.

Cosmetic skin care technology has evolved the use of various chemicals and enzymes to induce desquamation (exfoliation) of cutaneous cells in the superficial layer, the stratum corneum. This purportedly results in the gradual reduction of the skin's fine lines and an improvement in skin texture through the process of desquamation. Most of these preparations utilize one or more alpha hydroxy acids (AHA) for use as so-called chemical peels. These are generally administered by cosmetic or plastic surgeons, dermatologists or aestheticians, particularly when AHA concentrations are high, such as 30% or greater, with consequent low pH values and accelerated desquamation of corpus stratum with side effects of inducing production of free radicals in epidermis and dermis. In addition, many cosmetic products with less than 10% active AHA have been formulated in stable forms for home use. These may be purchased over the counter and are also sold by salons, cosmetologists, aestheticians, and drug stores as AHA-containing chemical peels. At these lower AHA concentrations they are more effective when used chronically, to achieve the desired goals.

The most effective AHAs are glycolic acid and lactic acid, but personal care products may also contain malic, citric, tartaric and gluconic acids. Glycolic acid is obtained from sugar cane, lactic from milk, malic from apples, tartaric from grapes, and citric acid from citrus fruits. A beta hydroxy, salicylic acid, is gaining some popularity too as it also exfoliates and has been helpful in acne-prone skin. AHAs absorb moisture from the atmosphere increasing also stratum corneum moisture and plasticity.

Some enzymes function as exfoliants that help break up or "dissolve" superficial skin cells. Exfoliation then allows skin to regenerate and thereby protect itself. These enzyme preparations are usually not irritating to the skin since they do not penetrate deeply. "Double dose" exfoliation may be accomplished by using these enzymes in masks or "scrub" preparations. Some of these enzyme cosmeceuticals are sold also with AHAs or antioxidants. The major enzymes used as topical exfoliants are obtained from papaya (papain), pineapple (ananase) or digestive enzymes from hog pancreas. Other preparations use various enzymes or proteins whose function is to block the body's natural enzymes (collagenase and elastase), which usually impair the skin by digesting connective tissue collagen and elastin fibers.

Chemosurgery, vernacularly known as "chemical peels," is a non-invasive technique which aims to restore wrinkled, blemished, unevenly pigmented ("brown age spots") or sun damaged facial skin. The professional or self administered procedures use chemicals in varying concentrations and at an acid pH values to "peel away" the skin's most superficial layers, the stratum corneum and the epidermis. The aim is for the "new" cells that form during the healing (repair) process to produce a smoother, tighter and "younger looking" skin surface. Chemical peels are not substitutes for surgical face lifts which eliminate sagging or excessive skin. Chemosurgery may be used for large surfaces, such as face and/or neck region or on specific areas such as forehead, under the eyes, or around the mouth.

Professionals employ three types of chemosurgery, namely chemical solutions containing phenol, trichloroacetic acid (TCA) and alpha hydroxy acids (AHA), the latter in higher concentrations than those available for home, chronic self use cosmetic type preparations.

Phenol full face peels are used to treat mainly coarse facial wrinkles, prominent brown age spots and chronic sun damaged skin, including some precancerous cutaneous growths. On the other hand, TCA peels are used primarily for fine surface wrinkles and superficial pigmentations. Results with TCA are less dramatic and shorter lasting, but may be repeated regularly and also used on the neck, in contrast to the more drastic phenol chemosurgery, which may cause scarring in the neck area.

Other techniques to reduce scarring for dermatologic conditions like acne and to eliminate the aged-skin appearance secondary to chronic photo-damage besides chemical (acid) peels have been employed. Dermabrasion uses physical means to accomplish desquamation, but purportedly despite its success rate has a number of complications, such as pigmentary changes and either atrophic or hypertrophic scarring. These may be ameliorated or reduced both in frequency after dermabrasion, which is so highly user dependent or intensity, by the post dermabrasion use of antioxidants, growth stimulating factors and melanocyte controlling compounds to render more normal post therapy dermatologic results.

Another technique which has been used by aesthetic surgeons and dermatologists is the thermal therapy applied via a continuous wave carbon dioxide laser. These lasers vaporize tissue ensuing in areas of variable but important degrees of thermal damage, also resulting in scarring. Although antioxidant preparations could ameliorate this dermal damage, this technique fortunately is being quickly replaced by so-called pulsed carbon dioxide lasers, a revolutionary approach in aesthetic surgery, but as all surgical techniques not fully devoid of bothersome and untoward cutaneous side effects and risks. True that pulsed $CO_2$ lasers selectively vaporize thinner layers of tissue and leave behind narrower zones of thermal damage, albeit free radicals are still elicited and cause their deleterious function on skin healing and scar promotion. Although these lasers improve substantially the wrinkling caused by photoaging, postoperatively, oozing and crusting develop for seven to fourteen days depending on the severity of the existing photodamage, the depth of the resurfacing laser procedure, and the individual's inherent capacity for wound healing. Although post-op moisturizers are ordinarily prescribed, the free radicals of this laser thermal injury should be combated with locally applied endogenous and exogenous antioxidants of this patent, as well as epidermal and/or fibroblast growth factors to enhance epidermal repair and wound healing, thus minimizing post-operative symptoms and skin appearance. In addition, erythema of the skin areas treated usually follows for six to eight weeks but may last for over three months after laser surgery, indicating persistent inflammation from the thermal burns of the novel pulsed $CO_2$ lasers. Hyper pigmentation and scarring may ensue in certain skin types, which may indeed be aborted or curtailed by use of these synergistic antioxidant preparations with the reparative skin growth factors, as outlined.

Indeed, some clinicians have recommended skin therapies be applied prior to laser therapy. With such applications, the skin will heal faster post laser surgery. Topical vitamin C and vitamin A, or its derivative, retinoic acid, should thus be employed. Studies indicate that the ascorbates as antioxidants, reduce pre-laser skin damage from solar radiation. Both putative nutrients promote production of collagen and aid treated skin to heal faster. Synergistic antioxidants, reparatives and epidermal growth factor will enhance this process and yield earlier therapeutic and more successful and acceptable clinical results.

Although the advent of the new $CO_2$ superpulsed lasers reduce occurrence of skin charring and scarring, patients still experience considerable signs and symptoms postoperatively. In lighter skin, patients exfoliating facial treatments (chemosurgery) are recommended weeks preoperatively to improve the cutaneous results of laser surgery. Occlusive dressings are applied post laser surgery for the first few days and on removal the treated area is seen as erythematous or pinkish-red reflecting the thermal burn and inflammation. This is the period to start cosmeceuticals, including moisturizers, antioxidants to diminish free radical damage, pigment preparations and epidermal growth factor to both normalize the reddened appearance of the new surfaced skin and to reduce the inflammatory reaction while stimulating epidermal cell growth and appearance of the immunologic Langerhans cells and melanocytes. The intent of this local treatment is to decrease symptoms and promote good, normal skin with avoidance of bothersome scars and hyperpigmentation. Pharmaceutical grade ingredients are preferred to reduce risk of skin irritation or other complicating cutaneous reactions and infections.

The skin repair processes are common to environmental, traumatic, surgical and dermatologic conditions. Cutaneous tissues so exposed to injury react so that water molecules contained within cells are altered and lipids of membranes or extracellular tissues are also injured which result in these etiologies in the formation of a number of noxious free radicals. The latter two conditions are known as the process of lipid peroxidation, which engender damaging lipid peroxides. In addition, there is a marked inflammatory cell response which also releases free radical species.

Ultraviolet B radiation exerts its most harmful effects when the sun is high on the horizon (high noon hours). In contrast, ultraviolet A radiation is more variable with time of day and time of the year making protection to UVA radiation a year round requirement. Sun care products should protect against both UVA and UVB radiation, and this needs to be considered in patients who have burns or have undergone any of the aforementioned therapeutic cosmetic procedures.

Ultraviolet radiation consists of short wave length, high energy UVB rays (290NM to 320NM) and longer wave length, lower energy UVA radiation (320NM to 400NM). The former is responsible for the range of sunburn damage from slight erythema to painful burns and blistering. These are acute phase effects. In contrast, UVA radiation penetrates the skin's deeper layers, epidermis and dermis, and is more responsible by its attack on collagen tissue for the so-called premature aging of skin or photoaging. Both UVA and UVB by their creation of free radicals may act synergistically on the pathogenesis of skin cancers, basal cell and squamous cell carcinomas and malignant melanomas.

Histopathologically, acute ultraviolet exposure which causes sunburn (so-called solar erythema) is associated with the development of altered epidermal cells becoming dyskeratotic and known as sunburn cells. Likewise, this UV injury has been shown to alter epidermal Langerhans cells which are essential in the cutaneous immune response, by activating helper T lymphocytes. Although accounting for only 2–4% of the epidermal cell populations, Langerhans cells are photodamaged by acute UV rays, and impair immune responses locally. Chemical burns and laser therapy likewise damage Langerhans cells. Epidermal cells have also been shown to become depleted of their reduced glutathione content from the aforementioned. In general, glutathione depletion in cells usually precedes cell injury and cell death, thus the importance of maintaining GSH levels intra-cellularly. Topical sunscreens ameliorate but do not prevent sunburn damage and contribute to photoaging of the treated skin, in addition to damage caused from the therapeutic chemical or thermal burns so applied.

During the process of phagocytosis by polymorphonuclear leucocytes (PMN), an increased consumption of oxygen occurs. This "respiratory burst" generates superoxide radicals ($O_2^-$), hydrogen peroxide ($H_2O_2$), the hydroxyl radical ($OH^-$) and hypochlorous acid (HOCl). Hydrogen peroxide is derived from the free oxygen species by a process called dismutation while, in the presence of catalytic iron, the hydroxyl radical peroxidizes polyunsaturated fatty acids in cell membranes.

In skin, oxygen radicals are also made by fibroblasts. Following radiation, chemical or thermal burns, there is an increased level of the enzyme xanthine oxidase in the skin, which also generates free oxygen radicals. These free radicals also have effects on gene activation during inflammatory processes in the skin, for they rapidly induce breaks in DNA. These genes encode transcription factors, which play roles in induction of cellular growth, differentiation and development.

The skin is a highly vascular organ, exposed to high levels of the ultraviolet rays, UVA and UVB, and atmospheric oxygen. The latter is essential for the genesis of oxygen free radicals, while the solar radiation is a most potent inducer through UV stimulation of the noxious cellular reactive oxygen species, reason for protecting skin post chemical or laser therapies.

Teleologically, the skin's surface has a well developed endogenous oxidant defense system to combat free radicals which include the enzymes superoxide dismutase, catalase and selenium dependent glutathione peroxidase as well as the ubiquitous thiol tripeptide, glutathione, in its reduced form. Also present in the epidermis are the nutritionally provided vitamins C and E, including the hydrophilic antioxidant dehydroascorbate and the lipophilic antioxidant alpha tocopherol, respectively.

Topical amino acid vitamin complex compositions have been proposed and are commercially available in cosmetic and pharmaceutical preparations. Thompson and co-workers patented some amino acids for various topical applications with vitamins B and E and cod liver oil, in U.S. Pat. No. 5,425,954, which is herein incorporated by reference. Amino acids enumerated in these products were arginine, isoleucine, leucine, methionine, phenylalanine, threonine and valine. These compositions were proposed as useful for burns, such as the thermal burns of laser therapy and the chemical burns of alpha and beta hydroxy acids and enzyme exfoliants, as well as cuts, incisions, abrasions, insect bites, inflammation from sun and wind exposure, psoriasis, eczema and seborrheic dermatitis. These amino acids purportedly promote normal epidermal cell function and cell maturation in rapidly dividing tissues, as in the aforementioned cutaneous conditions.

Ultraviolet radiation, particularly UVB, superimposes to the cutaneous therapies acute damage to the skin (sunburn) resulting in a cutaneous inflammatory response. Clinical symptoms include discomfort, pain, tenderness, itching, while local signs include erythema and edema. Skin inflammation associated with itching-results in scratching, which further traumatizes the treated and sunburned skin. This trauma causes bleeding into the affected tissues, such that hemoglobin is released from the red blood cells. As aforementioned, when the hemoglobin is exposed to the hydrogen peroxide generated from neutrophils and xanthine oxidase in inflamed tissues, there is hemoglobin degradation and consequent release of catalytic iron ions and toxic free heme which are themselves capable of initiating lipid peroxidation. These events in damaged skin aggravate the skin's inflammatory response, the exposed lesions of skin damage, and the consequent excoriations from the pruritus make these affected surfaces more likely to become infected by secondary bacterial contamination of the iatrogenic wounds, and the compounding damage from UV radiation. Thus, the importance of protecting the areas of treatment from the sun by protective garments, hats, sunglasses, sun blocking compositions and avoidance of maximum exposure to sunlight for as long as one year after chemosurgery or laser therapy.

It has been found that sunscreens alone are inadequate in protecting skin from UV radiation and in repairing skin so damaged. There are two types of sunscreens:

1. Reflectants which contain zinc oxide or titanium dioxide;
2. Absorbents, examples of which include P-aminobenzoic acid, benzophenone, methoxycinnamates and salicylates and many others well known in the state of the art of this industry.

Both groups protect against ultraviolet rays A and B radiation depending on the composition of the sunscreen, aiding the patient who has just undergone aesthetic procedures.

Melanins are a ubiquitous class of biological pigments, founds in the plant and animal kingdoms, mainly in skin, hair, eyes and feathers. In humans, melanins range in color from yellow to red-brown (pheomelanins) to brown and black (eumelanins). The latter include nitrogen containing pigments, produced by the enzymatic oxidation of tyrosine. The main building block of eumelanins is 5,6-dihydroxyindole. In contrast, the pheomelanins contain sulphur and differ biogenetically only in the availability of cysteine during the initial states of tyrosine oxidation. Melanin and the distribution of melanosomes in the epidermis are prime protectors of human skin from solar radiation. They thus play a role in photoprotection while epidemiologically proven to correlate with development of cutaneous malignancies.

Most evidence points to human cutaneous melanin as photoprotective, particularly from UVB radiation. Additional protection is provided by the stratum corneum, particularly towards erythema, solar elastosis and photocarcinogenesis. Melanin has a random distribution in the outer cutaneous layer and in the array of melanocytes in the basal cell layer. This natural photoprotection may be augmented by facultative pigmentation induced by UVB and UVA. Studies in humans with an end point of photoprotection include the number of sunburn cells, immunosuppression, erythema, melanogenesis and DNA damage.

Melanin products are produced and packaged by melanocytes which are specialized dendritic cells, found in the basal cell layer, between the epidermis and the dermis. Each melanocyte is surrounded by 36 keratinocytes and one Langerhans cell, denominated a melanin unit. Melanin syntheses takes place in organelles named melanosomes, which are transferred through the dendritic processes to the keratinocytes of each unit during pigmentary response to ultraviolet radiation.

Melanins have photoprotective properties and as well have been demonstrated to be free radical neutralizers and antioxidants. Melanin is a stable free radical whose status is enhanced by irradiation from sunlight, thereby increasing melanins ability to neutralize free radicals. In addition, melanin protects enzymes from free radical inactivation. The protective effect of melanin on the skin surface from exposure to the sun is due to the neutralization of free radicals, which are thermally and photochemically induced by the process of lipid peroxidation on the skin's unsaturated lipids. As an antioxidant, melanin protects against the oxidation of reactive molecules by molecular oxygen, producing a less toxic free radical. Melanin in this capacity acts synergistically with vitamin E.

Melanin confers photoprotection from the effects of UV rays, for sunburn erythema, actinic aging, and skin cancer. This protective role, especially against solar UVA has been compared to a neutral density filter. When melanin, however, is present with other well known sunscreen products, there is a synergistic increase in this photoprotection property. Melanin may also act as an aqueous dispersant for the sunscreen titanium dioxide.

Commercially available soluble melanin preparations have molecular weights ranging from 5,000 to 100,000, while colloidal melanin preparations range in particle size from 0.30 to 0.0150 UM. The highly anionic melanin biopolymer does not readily penetrate the skin in either of the above preparations. Its efficacy in serving these topical cutaneous functions depends on formulation strategies.

As an optional ingredient in these preparations, particularly in daytime compositions of creams, lotions or gels, melanin forms part of embodiment of this invention. Melanins will be incorporated in the appropriate concentrations, as is well known in the art of this industry, to render their photoprotective and free radical scavenging properties. These melanins are commercially available from suppliers such as Mel-Co, Orland, California and Tri Industries, Emerson, New Jersey.

Studies have shown that increases in intracellular GSH are beneficial. An L-cysteine delivery agent not only enhanced endothelial cell GSH concentration, but also protected these cells in an inverse, linear relationship from damage by endogenous hydrogen peroxide. This preventive role of GSH is of value in treating skin which has been treated by exfoliation, laser surgery and subsequently exposed to ultraviolet radiation following cosmetic therapy.

It is thus an object of the present invention to provide a composition useful in minimizing post therapy skin damage, as well as late and chronic complications from radiation induced photo damage which together may enhance or cause photoaging of the skin, nullifying the desired effects of cosmetic therapies employed.

It is yet a further object of the present invention to provide in the form of a topical carrier, certain antioxidants which are effective in reducing the lesions from burns, chemosurgery or laser therapy as well as secondary ultraviolet damage initiated by the formation of free radicals in the dermal layers.

It is yet a further object of the present invention to provide reparative epidermal growth factors to promote skin repair and wound healing from these aesthetic and surgical treatment modalities.

These and further objects will be more readily apparent when considering the following disclosure and appended claims.

SUMMARY OF THE INVENTION

The present invention deals with a composition and method for reducing the cutaneous effects and complications of chemosurgery and laser therapy of induced skin damage. The composition comprises an effective amount of a glutathione and selenoamino acid since selenium is the co-factor of glutathione peroxidase. The combination can be in the form of a lotion, cream, ointment, gel, spray, balm, emulsion or cosmetic foundation and can also include the further endogenous antioxidants acetyl L carnitine, melanins and superoxide dismutase as well as secondary exogenous components to be discussed hereinafter, plus the epidermal and/or fibroblast growth factors to aid in the tissue repair process by inducing orderly epidermal cell growth and maturation.

DETAILED DESCRIPTION OF THE INVENTION

As previously noted, the present invention deals with glutathione (GSH), in combination with selenium and thiol compounds used topically to act as free radical scavengers reducing skin changes and epidermal growth factors for enhancing repair. It is proposed that the described active ingredients be employed in topical compositions. Topical carriers are employed which should be both non-irritating to the skin and which are suitable for delivering the active components to the skin. Further, suitable topical carriers should be those which do not inhibit the antioxidant activity of the active ingredients thus reducing the efficiency of the composition for protecting the skin from the effects of acute and chronic ultraviolet radiation. Further, such carriers must be of sufficiently high purity and sufficiently low toxicity to render them suitable for chronic topical administration to the skin and be free of bacterial contaminants.

Certain antioxidants, particularly the endogenous L-glutathione and superoxide dismutase, as well as the element selenium, a co-factor for the enzyme glutathione peroxidase, and thiol compounds such as L-cysteine, can be employed in suitable carriers such as lotions, solutions, creams, ointments, foundation products, balms, sprays, aerosols or gels to protect and to treat the overlying skin surface in dealing specifically with the effects of the various free radicals on biornolecules, lipids, and cell membranes. Moreover, specific cellular growth factors, such as epithelial (epidermal) and/or fibroblast growth factors in appropriate concentrations and delivery vehicles, will be incorporated to these reparative preparations for accelerating healing of these wounds with quality repair.

Without being bound to any particular theory, it is noted that reduced glutathione is employed in protecting cells and aerobic organisms against oxidative stress by itself being oxidized. Thus, glutathione must act in combination with other enzyme systems in order to be reduced so that it may renew its role as a free radical scavenger. GSH functions also coordinately with the enzyme glutathione peroxidase to break down hydrogen peroxide and lipid hydroperoxides. Glutathione peroxidase in the body requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxide in the presence of reduced glutathione. This reaction reduces glutathione to oxidized glutathione (GSSG). In turn, the GSSG is reduced back to GSH by the enzyme GSH reductase thereby maintaining abundant cellular GSH to scavenge free radicals anew.

It is further contemplated that the present composition, as a preferred embodiment may include acetyl L carnitine. This latter component further participates in protecting cells against lipid peroxidation by locally increasing the amount of antioxidizing agents of GSH and ubiquinol. L-carnitine, also known as gamma trimethyl amino-beta hydroxy butyrate or Vitamin Bt occurs naturally in the body. It is a normal endogenous intermediary metabolite which has been identified in all mammalian cells and in blood and urine. It has the function of transporting fatty acids and other acidulated compounds across inner mitochondrial membranes and of maintaining the acyl CoA/free CoA ratio between the mitochondria and the cytosol of the cells. Acetyl L carnitine is the acetyl derivative of L-carnitine and is also a naturally occurring substance in the body as it provides a transport mechanism for the acetyl groups created by the beta oxidation of fatty acids while concomitantly regenerating acetyl co-enzymes in the cytosol of the cell.

Of interest herein, acetyl L carnitine has been shown to have a scavenging effect on the free superoxide anion. This antioxidant activity coupled by acetyl L carnitine's effect of inducing an increase in reduced glutathione and reduced ubiquinone levels provides a stabilizing effect on membranes by decreasing membrane lipid peroxidation. The skin is a highly vascular organ, extracellularly very rich in polyunsaturated fatty acids and thus prone to the process of lipid peroxidation. Thus, reduced glutathione and acetyl L carnitine in a topical preparation will act somewhat synergistically; the former as a reparative antioxidant which itself becomes oxidized and better able to be regenerated locally in its reduced form by the metabolic functions of acetyl L carnitine and by acetyl L carnitine's ability to enhance mitochondrial energy production. This is accomplished by the latter's actions on lipid metabolism and by the resulting increase in cytochrome oxidase, the final enzyme in the cellular respiratory chain.

Further, glutathione and selenium act synergistically in vivo as they are both constituents of the same enzymatic system. GSH serves as a specific donor substrate while selenium, provided from alimentary sources or locally from topically applied preparations of selenoamino acids, selenium yeast extracts or selenoamino acid chelates, provides the prosthetic group of GSH peroxidase, during its synthesis. The glutathione and selenium antioxidant functions are intrinsically related since by keeping a peroxidase in action, the GSH and selenium, contribute to the removal of the dismutation product of free oxygen radicals, namely, hydrogen peroxide. In a broad sense, GSH and selenium modulate free radical chains initiated or sustained by hydro peroxides.

Selenium is used in the present invention for its role as an antioxidant as well as its anticarcinogenic and antimutagenic properties. Selenium is an essential trace element, and a cofactor and constituent of the enzyme glutathione peroxidase. Selenium preparations as a sulfide have been used as topical antiseborrheic detergents (Selsun®) and in veterinary medicine topically for eczemas and dermatomycoses.

Selenomethionine decomposes lipid peroxides and inhibits in vivo lipid peroxidation in tissues of vitamin E deficient chicks. Other selenoproteins also show a high degree of inhibition of lipid peroxidation in hepatic tissues of various species, thus concluding that in vivo selenium has antioxidant behavior.

Extensive inflammation in an acute phase organ response induced by "burns." Free radical production is associated with inflammation and increased circulating lipid peroxides have been reported in burn patients. These parameters have been measured by urinary malondialdehyde levels as an indicator of lipid peroxidation. Supplemental oral antioxidants, such as vitamin E, and the trace elements which are directly involved in free radical scavenging, including selenium, zinc and copper, have been shown to have beneficial clinical effects and shorten hospitalization. The former acts as part of glutathione peroxidase while the latter two elements act as part of ceruloplasmin and superoxide dismutase. These trace elements also have site-specific antioxidant actions and, thus, the need to administer these locally at the site of the burn injury including chemical and thermal therapies for improved and accelerated wound repair.

Selenium has also been shown to affect the immune system. Selenium supplementation as 70% selenomethione in patients with psoriasis with normal pretreatment selenium blood levels showed in increase in blood 40% post treatment, although skin levels of selenium dependent glutathione peroxidase were unchanged in both normal and psoriatic skin. A statistically significant increase in the number of CD4+ T-cells was noted in the reticular dermis of the psoriatic lesions.

In other human studies, topical selenomethionine was investigated for its ability to reduce the degree of acute damage to the skin by sunburn as induced experimentally by ultraviolet irradiation. Eight women were treated for two weeks with lotion vehicle and then with three concentrations of selenomethionine (0.002%, 0.02% and 0.05%). The researchers found that topical selenomethione was effective in protecting against acute UV damage to the skin, as measured by the minimal erythema dose, using a multipbrt solar ultraviolet simulator. Plasma levels of selenium in these volunteers remained unchanged, suggesting the protective effect of the selenomethionine was locally at the skin.

The same investigators, Burke, K et al., conducted similar experiments in rodents to determine whether oral and/or topical selenomethionine supplementation could reduce the incidence of acute and/or chronic damage to the skin. This included sunburn and pigmentation as well as the development of skin cancers, respectively. These controlled studies showed that the concentration of selenium in skin in areas of topical application of the lotion containing selenomethionine were greater than those of the experimental animals given comparable oral doses. The selenium concentration of untreated skin and liver tissue were similar to those of animals receiving the oral selenium compound. There was no evidence of selenium toxicity in any of the experimental animals. The mice treated with selenomethionine had significantly less skin damage by ultraviolet irradiation, as indicated by reduced inflammation and pigmentation and by later onset and lesser incidence of skin cancers.

Selenium has been shown to be an effective inhibitor of skin tumor promotion in rodent skin, but the mechanism is not precisely known. Perhaps the common inciting factor by the carcinogens is the generation of toxic radicals. Selenium, as the co-factor of the enzyme glutathione peroxidase, detoxifies hydrogen peroxide and hydroperoxides within cells. This selenium-glutathione complex may lower the level of potentially damaging peroxide radicals that are generated from various carcinogenic promoting chemicals.

Selenium functions as an antioxidant, as stated, also by its role as a cofactor for glutathione peroxidase, a group of water soluble enzymes which also catalyze the destruction of both aqueous and membrane-bound hydroperoxides. In dietary selenium deficiency, these enzyme levels are markedly decreased resulting in severe free radical damage to the tissues so involved. The other related antioxidant systems cannot make up for depressed local activity or selenium and selenium dependent enzymes. Selenium deficiency also occurs after such injuries as burns and needs to be supplemented in these states, thus, the importance of providing selenium in these topical antioxidant preparations, as well as ascertaining adequate nutritional supplements.

"Cell growth stimulating compounds or factors" have been described as natural or exogenous compounds which have a stimulating effect on the elaboration and growth of specific cell lines. Specifically, in regard to promoting epidermal growth, such as in skin tissue repair or wound healing, various factors have been identified as growth factors, including epithelial (epidermal) growth factor (EGF), fibroblast growth factor (FGF), tissue respiratory factor (TRF), transforming growth factor (TGF) and insulin-like growth factor (IGF).

In the present formulations using antioxidants and other dermal nutrients and reparative compounds, one or more cell growth stimulating factors in suitable amounts effective for stimulating the growth of cells which encompass or surround and are injured or are responsible for healing wounds may be incorporated in the preparation of the present creams, balms, lotions, solution or gels, or other cosmetic compositions. Skin cellular reparative functions of dermatologic injuries or lesions (sunburn, thermal burns, radiation and laser burns, chemosurgery, dermatoses, etc.) are included in the list of therapies as examples.

A further active expedient is the use of epidermal growth factor. Epidermal growth factor (EFG) is an endogenous substances for the development and maintenance of the epidermis and dermis. EGF is a protein that catalyzes the cutaneous healing process by promoting epidermal and epithelial cells to divide and grow. It induces mitoses, so that skin constantly produces and uses EGF, particularly when skin is damaged, such as in ultraviolet radiation and after surgery, and trauma for both healing and reduction of scar and keloid formation. When applied topically, EGF generates and replaces epithelial cells. EGF also promotes synthesis of proteins, accumulation of collagen and formation of blood vessels. Following sunlight injury and during the aging process, topical application of EGF replaces the existing low levels of dermal growth factors to achieve improvement in the quality of the skin, thereby reducing sagging skin and wrinkles. The antioxidants protect and repair damaged skin from free radicals while the growth factors to be used in combinations will promote epidermal ell renewal and thus ensue in repair of affected tissues.

Epidermal growth factor is a 53 amino acid polypeptide which stimulates messenger RNA, DNA and protein synthesis. In vitro, it stimulates keratinocyte division and in vivo epidermal cell regeneration.

Epidermal growth factor (EGF) may be derived from various sources and is commercially available from specialized suppliers. Human EGF (hEGF) may also be produced from genetically engineered yeast, using the technique described by Brake et al., Alpha-factor directed synthesis and secretion of mature foreign proteins in *Saccharomyces cerevisae* (Proc. Natl. Acad. Sci-fi. USA 81:4642, 1984). EGF may also be derived from the submandibular glands of mice, so-called murine EGF. This factor may be isolated by the method of Savage and Cohen, as published in the Journal of Biol. Chemistry. 247:7609–7611, 1972.

In experimental animals, when applied to granulating wounds EGF has been shown to increase both the concentrations of DNA associated with cutaneous injury and of collagen hydroxyproline. In addition, other studies have been shown that when locally applied to fresh wounds, EGF accelerated the early phases of wound healing, as well as the quality of the repair. In humans, immunocytochemical techniques reveal the presence of EGF receptors within the cytoplasm of normal epidermis. In vitro studies confirm that EGF is sequentially processed within the cell's endosome. These studies also suggest that to yield a mitogenic signal, cells need to be exposed to EGF for about five hours, which may help to explain the "lag phase" in wound healing, by first achieving increases of DNA synthesis.

Normal regeneration of the epidermis after injury for healing of wounds requires mitosis and migration of the epidermal cells from residual epidermal appendages within the wound as well as from the intact epithelium surrounding the injury. Acceleration of epidermal regeneration may be enhanced by various agents as well as by epidermal growth factor (EGF). In vitro, this mitogenic effect requires continuous exposure of target cells to EGF. In their studies, Brown et al. (J. Expt. Med. 163, May: 1319–1324, 1986) administered human recombinant EGF mixed with topical creams. These were applied twice daily to animals with either partial thickness burns or split thickness epidermal burns. They noted a highly significant increase in the healing process of these wounds, purportedly due to the creams providing more continuous exposure of residual epidermal cells to the recombinant EGF. In this manner, EGF may stimulate the cells' mitotic activities for faster wound healing and improving the quality of the skin repair. The present patent application provides the synergistic antioxidant to reduce free radical injury complex coupled with EGF in cream, lotion, gel or other topical preparations to provide the active ingredients locally in order to enhance the repair process, as in the aforementioned clinical and investigative observations.

Thus, after cutaneous injury, residual epithelial cells proliferate in an organized fashion to regenerate an intact epidermis. Superficial wounds which do not result in total skin loss but retain at least a portion of the dermal layer, heal primarily by this process of epidermal regeneration. Epidermal growth factor induces replacement of cells by inducing mitosis. Many experiments, animal and human studies, have positively shown the beneficial effect of EGF in the process of wound repair. These clinical situations include partial thickness burns, skin graft donor sites, and chronic skin ulcers. It is also of use in healing radiation skin burns, surgical scars and in the repair process of cosmetic surgeries and cutaneous chemical peels.

Also useful herein is a component known as Tissue Respiratory Factor (TRF). TRF is a live yeast cell derivative which has been used in over the counter pharmaceutical preparations since patented in the 1940's and more recently as an ingredient in cosmetics. It is commercially available (Brooks Industries, Biodynes-TRF, South Plainfield, N.J.) and purported to be a powerful internal moisturizer which refreshes dry and infirm skin. TRF was first used as an anti-hemorrhoidal product (Preparation H, Whitehall Laboratories). TRF is composed of low molecular weight glycosidic/peptide fractions, with a ratio of 1:3. The residual glycopeptide linkages are through the amino acid asparagine residues. Because TRF is prepared from live yeast cell derivatives, additional trace quantities of coenzymes, vitamins, amino acids and minerals, characteristic of yeast species, are available in these extracts, which enhance the therapeutic capabilities of TRF in these pharmaceutic/cosmetic preparations.

TRF has a maximum absorbance of 13.0–20.0; ultraviolet spectrophotometer of a 1% TRF filtered solution reads at 256–258 NM. It is available as a water soluble material for gels, emulsions, lotions and creams. TRF has been shown to promote wound healing through its ability to increase fibroblast synthesis of collagen and elastin fibers resulting in smoothing of the skin. TRF's moisturizing effect is accomplished by increasing uptake of moisture by nascent protein and increasing oxygen utilization in the skin. TRF has been used in the treatment of sunburned skin and has been preferred for decreasing pain and discomfort of sunburn damaged skin when compared to a topical post-sun product containing the local anesthetic benzocaine. Thus, TRF, as other growth factors, may be used in combination to these proposed antioxidant preparations as a preventive and prophylactic agent to photodamaged, burned, incised, irradiated or inflamed skin of diverse etiologies.

Yeast extracts with mineral glycopeptides, such as selenomethionine or zinc glycopeptide as well as tissue respiratory factor have already been mentioned as essential components to these preparations. An additional product which may be part of the active ingredients of these compositions are sulphur rich yeast extract compounds, also commercially available (example: Clariskin, R.I.T.A. Corporation, Woodstock, Ill.). This material is extracted from the cytoplasm of eukaryotic cells of *Saccharbmyces cerevisiae*. These sulphur rich yeast extracts purportedly aid in the diminution or elimination of dermatologic "brown age spots" by diverting the process of melanogenesis toward the synthesis of lighter colored pigments in the skin. The reduction of brown melanin production is accomplished through the sulphur rich antioxidant, glutathione, and the associated enzyme, glutathione reductase. The latter enzyme is present in this yeast depigmenting extract and its intracellular function is to reduce glutathione (GSSG) that has already been oxidized in its role as an antioxidant as reduced glutathione (GSH). This reeaction can be shown as

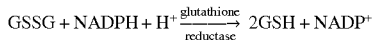

The local relative or excess of reduced glutathione (GSH) and other thiol compounds in these cosmetic preparations participate in metabolic reactions by diverting the syntheses of melanocytic pigments, inhibiting the dark pigments (eumelanin) in favor of the biosynthetic pathway toward the clear pigments (pheomelanin). In addition, the glutathione reductase, as aforementioned, participates in the enzymatic reaction toward production of GSH, thus enhancing the anti-free radical activity of these complex and synergistic compounds.

The skin's "brown spots" are a result of over production of melanin by a specific cell called melanocyte. Although these cells tend to decrease in numbers in the mid-third decade of life, research has revealed that they tend to accumulate in body areas exposed to solar radiation hence localized hyperpigmentation of these areas, particularly the face, neck and hands. Repeated exposure to the sun's ultraviolet rays and the inherent aging process of skin cause these "brown age spots" to appear on exposed skin surfaces. Thus, this patent application for use of synergistic compounds in promoting and enhancing locally the body's, especially the skin's, defense mechanisms to free radical species. Glutathione, as GSH, plus the co-factor selenium of the enzyme glutathione peroxidase, plus thiol compounds and glutathione reductase of this yeast extract complete the body's prime antioxidant components, the glutathione cycle. These preparations, plus other key antioxidants and skin repair factors are able to both prevent and chain break free radical reactions in tissues and cells, concomitantly helping repair the skin or heal the wound, created by chemosurgery, laser therapy, burns and complications of the various etiologies so enumerated.

Thiol rich yeast extracts also provide glutathione peroxidase and the sulphur groups to promote its synthesis and enhance the glutathione pathways.

Beta glucans may be derived from plant based polysaccarides and have been known to stimulate macrophages, thereby activating non-specifically the immune system. Polymers belonging to the beta 1–3 glucan family have been purified from extracts of yeast wall (*Saccharomyces cerevisiae*). Beta glucans protect the skin's immunocompetent Langerhans cells from an inhibitory effect from ultraviolet rays. Thus, beta glucans are photoprotective and also have free radical scavenging activities and anti-inflammatory properties. These polysaccharides have also been shown to stimulate collagen and are synergistic in their functions with ascorbic acid. Beta glucans are commercially available from a number of suppliers, including Alban Muller International, Emerson, N.J. Recommended doses of the concentrate in water and sorbitol are at 0.01 to 0.1 percent, until 2.0 percent for anti-inflammatory activity comparable to a 0.1% hydrocortisone preparation. The free radical scavenging activity of this preparation in powder form requires a concentration of 0.015% to 0.045% to inhibit hydroxyl radicals. Other beta glucan preparations are available for inclusion in these reparative and solar protective compositions, such as microat uvax, from Nurture, Inc., Missoula., Mont. and Betavera from Brooks Industries, South Plainfield, N.J.

As noted previously, the active ingredients described above can be incorporated in any suitable pharmacologically acceptable carrier which is suitable for topical administration to the human skin. As such, the pharmacologically acceptable carrier must be of sufficient purity and have sufficiently low toxicity to rerider it suitable for administration to a human noting that, typically, the carrier can represent up to 99.99% and typically from at least approximately 80% of the total composition.

Typical compositions for use herein include a wide variety of physical forms. These include, but are not limited to, solutions, lotions, creams, oils, gels, sticks, sprays, ointments, balms and pastes. Generally, such carrier systems can be described as being solutions, emulsions, gels, solids and aerosols.

Solvents are generally employed in the preparation of suitable topical compositions. Such solvents can either be aqueous or organic based and, in either case, the solvent must be capable of having dispersed or dissolved therein the above-described active components while not being irritating to the user. Water is a typical aqueous solvent while suitable organic solvents include propylene glycol, butylene glycol, polyethylene glycol, polypropylene glycol, glycerol, 1,2,4-butanetriol, sorbitol esters, 1,2,6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is incorporated by reference.

Alternatively, the present composition can be formulated as a lotion containing from about 0.01% to 10% of the above described active ingredients. Further, the product.can be formulated from a solution carrier system as a cream. A cream of the present invention would preferably comprise from about 0.1% to 15% and preferably from 1% to 5% of the above described active ingredients. Lotions and creams can be formulated as emulsions as well as solutions.

It is contemplated that as one embodiment, the active ingredients described above be used as a lotion or cream emulsion of the oil-in-water type or as a water-in-oil type, both of which being extremely well known in the cosmetic field. Multi-phase emulsions such as the water-in-oil type is disclosed in U.S. Pat. No. 4,254,105, the disclosure of which is incorporated herein by reference.

It is further contemplated that the active ingredients of the present invention be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 99% of an emollient plus to about 0.1% to 99% of a thickening agent. Reference is again made to U.S. Pat. No. 5,296,500 and the citations contained therein for a more complete disclosure of the various ointment, cream and lotion formulations for use herein.

It is important to supply locally both glutathione and the synergistic antioxidants to restore epidermal glutathione levels and enhance the reparative antioxidant chain breaking reactions. It becomes imperative to prevent UV ray damage by prophylaxis with skin care (sun protection) products and appropriate clothing, plus the prevention of free radicals and their neutralization by locally applied chain-breaking antioxidant preparations, as proposed in the present application.

EXAMPLE 1

A composition containing the following ingredients was prepared in making a reparative hand and nail formula.

| Ingredients | Percentage by Weight |
| --- | --- |
| water | 56.3844 |
| hydroxyethylcellulose | 0.735 |
| EDTA | 0.084 |
| carbomer ETD 2050 | 0.095 |
| water for carbomer slurry | 6.025 |
| PEG 7 glycerol cocoate | 0.14 |
| canola oil | 12.64 |
| squalane oil | 0.62 |
| cetearyl alcohol ceteareth 20 | 0.21 |
| cetearyl alcohol polysorbate 60 | 0.4 |
| stearic acid | 3.098 |
| cetyl alcohol | 2.246 |
| cetyl ricinolate | 1.788 |
| phenyldimethicone | 0.99 |
| PEG 10 soya sterol | 0.136 |
| sesame oil | 2.22 |
| cocoa butter | 0.831 |
| sodium hydroxymethylglycinate | 0.4 |
| lecithin | 0.02 |
| sodium PCA | 0.25 |
| marine algae | 5.88 |
| sodium hyaluronate | 0.14 |
| peppermint oil | 0.32 |
| sodium lactate | 0.0376 |
| lactic acid | 0.012 |
| honey | 0.34 |
| dex-panthenol (vitamin B5) | 1.037 |
| thiol yeast extract | 0.22 |
| ascorbyl palmitate (with canola oil) | 0.5 |
| pseudo collagen | 0.2 |
| retinyl palmitate & choleciferol | 0.25 |
| carrot oil | 0.08 |
| zinc glycopeptide | 0.165 |
| serum albumin | 0.1 |
| sodium hydroxymethylglycinate | 0.121 |
| threonine | 0.03 |
| green tea | 0.06 |
| L-glutathione | 0.03 |
| superoxide dismutase | 0.03 |
| selenomethionine | 0.03 |
| epidermal growth factor | 0.25 |

In preparation, charge vessel with water, disperse EDTA followed by hydroxyethylcellulose and gradually heat to 65 degrees C. Separately disperse carbomer ETD 2050 into water for-carbomer slurry and add to heated EDTA and hydroxyethylcellulose and when uniform add PEG 7 glycerol cocoate. Heat canola oil, squalane oil, cetearyl alcohol ceteareth 20, cetearyl alcohol polysorbate 60, stearic acid, cetyl alcohol, cetyl ricinolate, phenyidimethicone, PEG 10 soya sterol, sesame oil and cocoa butter to 75° C. and add to the mixture above mixing or homogenizing for uniformity. Add sodium hydroxymethylglycinate followed by lecithin, slowly cool to 40° C. and add sodium PCA, marine algae, sodium hyaluronate, peppermint oil, sodium lactate, lactic acid, honey, dex-panthenol (vitamin B5) and thiol yeast extract. Continue to cool to 30° C. and add the remaining ingredients, ascorbyl palmitate (with canola oil), pseudocollagen, retinyl palmitate & choleciferol, carrot oil, zinc glycopeptide, serum albumin, sodium hydroxymethylglycinate, threonine, green tea, L-glutathione, superoxide dismutase, selenomethionine, epidermal growth factor.

EXAMPLE 2

A composition using the following ingredients was prepared in making a reparative lotion.

| Ingredients | Percentage by Weight |
| --- | --- |
| water | 71.781 |
| disodium EDTA | .08 |
| hydroxyethylcellulose | 0.74 |
| EDTA | 0.084 |
| carbomer ETD 2050 | 0.067 |
| water | 3.33 |
| PEG 7 glycerol cocoate | 0.105 |
| cetyl alcohol | 2.114 |
| glyceryl stearate, PEG 100 stearate | 0.379 |
| sesame oil | 1.52 |
| canola oil | 8.65 |
| phenyldimethicone | 0.94 |
| cocoa butter | 0.56 |
| PEG 10 soya sterol | 0.12 |
| squalane oil | 0.095 |
| cetyl ricinoleate | 0.12 |
| triethanolamine 99% | 0.305 |
| lecithin | 0.054 |
| sodium hydroxymethylglycinate | 0.07 |
| niacinamide | 0.09 |
| green tea | 0.03 |
| echinacea | 0.047 |
| sodium hyaluronate | 0.16 |
| sodium lactate | 0.035 |
| lactic acid | 0.0018 |
| seaweed | 2.13 |
| dex panthenol (vitamin B5) | 0.714 |
| arnica oil | 0.096 |
| epiermal growth factor | 0.096 |
| ascorbyl palmitate in canola oil | 0.284 |
| honey | 0.29 |
| NaPCA | 0.16 |
| zinc glycopeptide | 0.048 |
| diazolidinyl urea, methyl paraben, propyl paraben and propylene glycol | 1.0 |
| carrot oil | 0.0392 |

In preparation, add disodium EDTA to water (71.781%). Add hydroxyethylcellulose to mixture and slowly raise water temperature to 65° C. When hydroxyethylcellulose is dispersed and has thickened, add pre-mixed carbomer ETD 2050 and water (3.33%). Heat water, PEG 7 glycerol cocoate, cetyl alcohol, glyceryl stearate, PEG 100 Stearate, sesame oil, canola oil, phenyidimethicone, cocoa butter, PEG 10 soya sterol, squalane oil and cetyl ricinoleate to 75° C., add to water phase when water phase is fully dispersed and uniform, mix well for at least 5 to 10 minutes and briefly homogenize if necessary, keeping temperature at 58° to 60° C. during mixing. Add triethanolamine 99% and mix for 5 minutes. Add lecithin and slow mixer down. Start cooling to 50° C. and then add items sodium hydroxymethylglycinate and niacinamide. Mix slowly to 40° C., then add green tea, echinacea, sodium hyaluronate, sodium lactate, lactic acid, seaweed, dex panthenol (vitamin B5), arnica oil, calendula oil, ascorbyl palmitate in canola oil, honey, NaPCA and zinc glycopeptide. Cool to 30° C., then add remainder of ingredients.

EXAMPLE 3

A composition containing the following ingredients was prepared in making a protein gel masque.

| Ingredients | Percentage by Weight |
| --- | --- |
| hydroxyethylcellulose | 1.33 |
| water | 77.1 |
| water | 9.5 |
| carbomer | 0.18 |
| PEG 7 glycerol cocoate | 0.15 |
| dex panthenol (vitamin B5) | 0.88 |
| sodium hydroxymethylglycinate | 0.53 |
| zinc glycopeptides | 0.11 |
| marine algae | 3.88 |
| ascorbyl glucosamine | 0.02 |
| sodium PCA | 0.5 |
| serum albumin | 0.6 |
| plant pseudocollagen | 0.7 |
| sodium hyaluronate, hydrolyzed glycosaminoglycans | 1.5 |
| thiol yeast extract | 2.0 |
| lecithin | 0.02 |
| sodium lactate | 0.07 |
| honey | 0.33 |
| green tea | 0.06 |
| L-glutathione | 0.03 |
| superoxide dismutase | 0.03 |
| selenomethionine | 0.03 |
| epidermal growth factor | 0.25 |

In preparation, mix and heat to 50° C. hydroxyethylcellulose and water (77.1%) until gum thickens. Add water (9.5%) and carbomer together until all carbomer is dispersed, then add hydroxyethylcellulose and water mixture. Add sodium hydroxymethylglycinate and cool to 30° C. At 30° C. on slow agitation, add remainder of the ingredients including dex panthenol (vitamin B5) in the order listed above.

EXAMPLE 4

A composition using the following ingredients was prepared to make a sunburn lotion.

| Ingredients | Percentage by Weight |
| --- | --- |
| water | 70.136 |
| disodium EDTA | .08 |
| hydroxyethylcellulose | 0.74 |
| carbomer ETD 2050 | 0.067 |
| water | 2.801 |
| PEG 7 glycerol cocoate | 0.105 |
| cetyl alcohol | 2.114 |
| glyceryl stearate & PEG 100 stearate | 0.379 |
| stearic acid | 3.209 |
| sesame oil | 1.52 |
| canola oil | 8.65 |
| phenyldimethicone | .094 |
| cocoa butter | 0.56 |
| PEG 10 soya sterol | 0.12 |
| squalane | 0.095 |
| cetyl ricinoleate | 0.12 |
| triethanolamine 99% | 0.305 |
| lecithin | 0.054 |
| sodium hydroxymethylglycinate | 0.07 |
| niacinamide | 0.09 |
| green tea | 0.03 |
| echinacea | 0.047 |
| sodium hyaluronate, hydrolyzed glycosaminoglycans | 0.16 |
| sodium lactate | 0.035 |
| lactic acid | 0.0018 |
| marine algae | 2.13 |
| dex panthenol (vitamin B5) | 0.714 |
| arnica oil | 0.096 |
| calendula oil | 0.096 |
| vitamin C (ascorbyl palmitate) in canola oil | 0.284 |
| honey | 0.29 |
| NaPCA | 0.16 |
| zinc glycopeptide | 0.048 |
| diazolidinyl urea, methyl paraben, propyl paraben | 1.00 |
| carrot oil | 0.0392 |
| retinyl palmitate, cholecalciferol | 0.06 |
| selenium yeast extract | 0.11 |
| L-glutathione | 0.03 |
| superoxide dismutase | 0.03 |
| selenomethionine | 0.03 |
| epidermal growth factor | 0.25 |
| micronized titanium dioxide | 3.00 |
| benzophenon, NE3 | .05 |
| fragrance may be added if desired | |

In preparation, mix EDTA into water (70.136%) at 60° C. and then add hydroxyethylcellulose. Add carbomer ETD 2050 to water (2.801%) and completely dissolve, add to water and hydroxyethylcellulose mixture. Add PEG 7 glycerol cocoate to water mixture. Heat to melt cetyl alcohol, glyceryl stearate & PEG 100 Stearate, stearic acid, sesame oil, canola oil, phenyidimethicone, cocoa butter, PEG 10 soya sterol, squalane and cetyl ricinoleate to a temperature of 65° C., then add to water phase, keeping temperature of water phase at 60° C. during mixing. Add triethanolamine 99% and mix for 5 minutes. Add lecithin and slow mixture down, start cooling to 50° C. and then add sodium hydroxymethylglycinate and niacinamide at a slow mix. Continue to mix slow and bring temperature to 40° C., then add dex-panthenol (vitamin B5). Cool down to 30° C. and add green tea, echinacea, sodium hyaluronate, hydrolyzed glycosaminoglycans, sodium lactate, lactic acid, marine algae. Then add the remainder of the ingredients.

EXAMPLE 5

An aerosol formulary concentrate can be produced according to the following formula.

| Ingredients | Percentage by Weight |
| --- | --- |
| water | .010 |
| vitamin B5 | .010 |
| vitamin C ascorbic acid | .002 |
| glycerin | .010 |
| isopropyl myristate | .011 |
| dipropylene glycol | .051 |
| alcohol | .920 |
| superoxide dismutase | .0003 |
| acetyl-carnitine HCL | .0003 |
| selenomethionine | .0003 |
| green tea | .0060 |
| epidermal growth factor | .0025 |
| propellant (60:40) 114/12 | .30 |
| concentrate | .70 |

EXAMPLE 6

A sun gel can be produced according to the following formula.

| Ingredients | Percentage by Weight |
| --- | --- |
| hydroxyethylcellulose | 1.33 |
| water | 79.275 |
| water | 11.7 |
| carbomer | 0.15 |
| PEG 7 glycerol cocoate | 0.18 |
| dex panthenol (vitamin B5) | 0.88 |
| sodium hydroxymethylglycinate | 0.53 |
| zinc glycopeptides | 0.11 |
| marine algae | 1.00 |
| sodium PCA | 0.5 |
| sodium hyaluronate, hydrolyzed glycosaminoglycans | 1.5 |
| selenium yeast extract | 0.08 |
| lecithin | 0.02 |
| sodium lactate | 0.07 |
| honey | 0.33 |
| green tea | 0.06 |
| L-glutathione | 0.03 |
| superoxide dismutase | 0.03 |
| selenomethionine | 0.03 |
| phynylbenzimidazole sulfonic acid | 2.00 |
| water soluble sunscreen | 0.17 |
| epidermal growth factor | 0.25 |

In preparation, mix and heat to 50° C. hydroxyethylcellulose and water (79.275%) together until gum thickens. Add water (11.7%) and carbomer together until all carbomer is dispersed, then add first water phase. Add sodium hydroxymethylglycinate and cool to 30° C. At 30° C. and on slow agitation, add remainder of the ingredients in the order given.

EXAMPLE 7

A suitable composition for use of the present invention as a reparative cream is as follows:

| Ingredients | Percentage by Weight |
| --- | --- |
| water | 59.751 |
| hydroxyethylcellulose | 0.8 |
| EDTA | 0.09 |
| glycerol cocoate | 0.14 |
| sesame oil | 8.73 |
| canola oil | 5.98 |
| squalane oil | 0.95 |
| cetearyl alcohol & ceteareth 20 | 0.215 |
| cetearyl alcohol & polysorbate 60 | 0.254 |
| stearic acid | 3.099 |
| cetyl alcohol | 2.348 |
| cetyl ricinoleate | 1.787 |
| phenyldimethicone | 1.062 |
| PEG-10 soya sterol | 0.122 |
| cocoa butter | 0.84 |
| triethanolamine 99% | 0.29 |
| lecithin | 0.02 |
| sodium PCA | 0.27 |
| seaweed | 5.54 |
| sodium hyaluronate | 0.193 |
| marigold | 0.2 |
| sodium lactate | 0.038 |
| lactic acid | 0.018 |
| honey | 0.452 |
| vitamin B5 | 1.038 |
| vitamin B complex | 0.215 |
| vitamin C and oil mix | 1.226 |

-continued

| Ingredients | Percentage by Weight |
| --- | --- |
| pseudo Collagen | 0.93 |
| vitamins A and D3 | 0.7 |
| carrot oil | 0.09 |
| zinc glycopeptide | 0.17 |
| serum albumin | 0.857 |
| Germaben II ® (propyleneglycol, diazolidinyl urea, methyl paraben, propyl paraben) | 1.065 |
| glutathione | 0.03 |
| selenomethionine | 0.03 |
| acetyl L carnitine HCL | 0.03 |
| green tea | 0.06 |
| superoxide dismutase | 0.03 |
| carbomer | 0.09 |
| epidermal growth factor | 0.25 |

As noted from the above, although applicant can employ commercially available selenium containing selenoamino acids such as L-selenomethionine such as those described in U.S. Pat. No. 4,865,840, the disclosure of which is incorporated by reference herein, applicant can also use as its selenium source, a selenium yeast extract. The proposed preparations may be used alone or in combination with essential mineral glycopeptides. These compounds are elaborated in the laboratory by feeding the putative metal ions to living yeast cultures by standard microbiologic techniques. The yeast organisms are able to incorporate the minerals as complexes within the cellular glycoproteins.

These complexes are mineral yeast extracts and are commercially available from suppliers such as Brooks Industries, Plainfield, N.J., Pharmachem, South Hackensack, N.J. and Triarco, Patterson, N.J. The mineral-yeast extracts include the following, alone, or in combination with calcium, copper, germanium, iron, manganese, magnesium, selenium, silicon and zinc. These glycopeptides containing one or more of the aforementioned minerals have been shown to possess less toxicity and increased penetration into the skin. Mineral amino acid chelates may also be used and are widely available from commercial suppliers.

The mineral selenium containing yeast extract, as noted above, is prepared similarly by feeding the selenium to living yeast cultures. Preparations of selenium yeast extract as Se-glycopeptide, are available as clear, low odor, filtered solutions. These have been shown to have moisturizing, toning and skin revitalizing properties. The selenium yeast extract penetrates into the skin and the selenium participates in its usual metabolic activities, including acting as a co-factor for the enzyme glutathione peroxidase. The addition of selenium yeast extract to these topical preparations enhances these as it synergizes with reduced glutathione and other antioxidants.

As further noted from several of the examples, the present invention further contemplates the use of additional optional expedients, for example, superoxide dismutase (SOD). SOD is a ubiquitous cellular enzyme whose main function is in protecting cells against oxidative stress. Superoxide dismutases are a family of cytosolic metaloenzymes which specifically remove free oxygen radical ($O_2^-$). There are three distinct forms of SOD, namely, CUZN SOD, MN SOD and extracellular SOD (EC-SOD) which is a copper enzyme located on endothelial cell surfaces. The differences in the SODs is in their aminoacid sequences as well as location at their active sites of the transition metals. It is hypothesized that the enzyme SOD, along with glutathione peroxidase and its selenium cofactor are effective preventive antioxidants because they eliminate molecules involved in the initiation of free radical reactions. SOD also protects intracellular reduced glutathione against radical mediated chain oxidation as the combination of SOD and reduced glutathione prevents redox cycling reactions.

It is also contemplated that, as a further optional expedient that the present composition optimally contain from approximately 0.01% to 10% Japanese green tea. Chemically, extracts of Japanese green tea have been analyzed and characterized. Active ingredients include caffeine, theobromine, theophylline and xanthines which, together, have been shown to reduce irritation of the skin, including that caused by various alpha hydroxy acids and other ingredients in cosmetics, thus making green tea an important supplement in topical cosmetic and dermatological preparations. Green tea also contains potent polyphenols, catechin compounds which effectively act as antioxidant agents to scavenge for radicals. The main catechin constituent of green tea is (−)epigallo catechin gallate (EGCG). It has also been shown that EGCG inhibits hydrogen peroxide formation by human leukocytes, the first cell in the inflammatory cellular response to injury. EGCG is of value to function synergistically as an exogenous antioxidant in these topical preparations with the active ingredients comprised of endogenous antioxidants.

In a preferred embodiment, the compositions of the present may be enhanced by the addition of zinc salts. Zinc may function by its healing properties on wounds, particularly as zinc oxide, and also to render the present preparations odorless, presumably by removing traces of hydrogen sulfide, which could emanate from sulfur groups used in these preparations. Zinc may also be administered as one of the trace metals prepared in yeast extracts as mineral (zinc) glycopeptides.

Compositions preferably comprise from about 0.001% to about 8% of a zinc salt, more preferably from about 0.01% to about 4%, more preferably still from about 0.1% to about 0.5%.

Zinc, the second most abundant trace metal in the human body and present in all living cells and body secretions, was identified as a trace metal by Ravlin in 1869.25% of total body zinc content is found in the skin mainly as zinc metaloenzymes. For over 3000 years, zinc in the form of zinc oxide or calamine, has been used in the treatment of wounds. Zinc is still used in castor oil and as zinc oxide for treatment of "diaper rash" and in a vast number of zincated bandages, dressings and creams.

It has more recently been shown that zinc metaloenzymes in the skin have a prominent role in the reconstruction of the wound matrix. Zinc, along with copper is necessary for cross-linking of collagen fibers in the skin repair process. Although zinc probably plays a role in all stages of healing, zinc concentrations increase at the margins of the wound during the formation of granulation tissue, re-epithelialization and norrmalization periods, whereas cutaneous calcium requirements are greater during hemostasis and inflammation. The concentrations of zinc in the margins of the wound during repair are 15–20% higher than in contiguous intact skin and are provided from zinc in blood. Since zinc thus is of value in the skin healing process as shown in experimental animals and in clinical studies with zinc oxide, the addition of zinc as an ingredient to these preparations will promote healing and enhance the repair process following chemosurgery or laser therapy.

Like the same tissue and cellular damage produced by radiation and burns, oxidant by products of normal metabolism cause extensive damage, as stated, to cells, membranes, DNA, proteins and lipids. Anti-oxidants, as endogenous enzymes and scavenger molecules, like GSH, act as defenses against this oxidant damage. Other exogenous molecules such as the ascorbates and tocopherols also assist in these defense mechanisms acting synergistically with glutathione to effect preventive and reparative mechanisms to oxyradical damage.

These cosmeceutical preparations provide these vitamins in sufficient concentrations to exert locally their physiologic and pharmacologic properties.

Vitamin E, particularly in its alpha-tocopherol moiety, has been employed to inhibit oxidation of oils and fats in foods, cosmetic preparations and drugs. Vitamin E is not only an anti-oxidant but also has anti-inflammatory properties. In skin, vitamin E levels are present in dermis and epidermis, but are depleted by malnutrition and by ultraviolet light, thus their importance too in providing these to act in vivo as antioxidants, and thereby protecting affected and new skin cells. Vitamin E moisturizes and enhances skin smoothness. It is soothing and also participates in skin repair and wound healing.

Cell membranes and plasma lipoproteins contain alpha tocopherol, which is a lipid soluble molecule that functions as a chain breaking (reparative) anti-oxidant. An —OH attached to the hydrophobic structure of tocopherol easily releases its hydrogen atom, so that peroxyl and alkoxyl free radicals generated during lipid peroxidation then may combine with this anti-oxidant instead of with adjacent fatty acid side chains, thereby terminating this chain reaction process of lipid peroxidation. Experimental evidence shows that the tocopherol radical migrates to the membrane surface. It is then reconverted to alpha tocopherol by its reaction with ascorbic acid (vitamin C). Thus vitamins E and C are synergistic and minimize the toxic effects on lipid peroxidation in cell and basement membranes and lipoproteins. Moreover, glutathione and selenium also act synergistically with vitamin E, the former GSH, by regenerating alpha tocopherol from its tocopheroxyl radical form. Also, vitamins C and E, selenium and glutathione, in experimental animals, have been shown to work together as anti-oxidants.

Ascorbic acid, vitamin C, plays a significant role in skin metabolism and in synthesis of collagen as a co-factor in hydroxylation reactions for the formation and function of collagen. High vitamin C levels not only stimulate collagen but also reverse epidermal thinning and offer skin protection against ultraviolet rays. These properties of vitamin C are enhanced by using ascorbyl glucosamine where the polyamine complex protects the ascorbic acid, enhancing the antioxidant and anti-collagenase properties of these products. It is commercially available from Collaborative Laboratories, East Setauket, N.Y.

Vitamin C, a water soluble small molecule anti-oxidant, is located in aqueous phases of cells while, as noted, vitamin E is in the lipid portion of membranes. Together they protect lipids and lipid structures against peroxidation. Vitamin C repairs the tocopheroxyl radical and permits that molecule to function again as a tocopherol free radical chain-breaking anti-oxidant. The ascorbate free radical produced in this reaction with tocopherol can be removed from the tissues by a dismutation reaction. The dehydroascorbate and the ascorbate radical can then be removed by enzyme-systems that use NADH or NADPH as sources of reducing molecules. Thereby, ascorbate is recycled to protect again the process of lipid peroxidation by its synergistic function with vitamin E.

Thus, these topical preparations will, in their preferred form, contain mixtures of vitamins C and E to enhance locally the anti-oxidant activities of the active ingredients, particularly in their function as chain-breaking anti-oxidants in lipid peroxidation.

The present invention also contemplates, as an optional expedient, the inclusion of vitamin A which occurs only in animal organisms and is not found in plants. It is usually extracted from liver oils, mainly in its esterified forms but may also be synthesized in the laboratory. The liver converts carotenoids, particularly beta-carotene, into vitamin A which particularly vitamin A palmitate (retinyl palmitate), may be used in these preparations, more in concentrations from 0.001 to 1% but more preferably from 0.005 to 0.09%. Retinyl palmitate, a common ingredient in cosmetics, is essential for normal skin, nail and hair development. It increases skin elasticity and promotes thickening of the epidermis and dermis.

Beta-carotene, which is pro-vitamin A, is found in many plants and is a nutrition source and the main coloring matter in carrots and egg yolks. B-carotene is used in cosmetics as a coloring agent and also as a source to the body of vitamin A. Carotene, like vitamin A compounds, may be absorbed by the skin. Carotenoids, including beta-carotene, are small molecule dietary and topical anti-oxidants. Carrot oil is rich in vitamin A and carotenoids and may be used in these preparations in a concentration between 0.001% and 1% as a source of these molecules. It is a light yellow essential oil derived from seeds of carrots and has no known toxicity. Carrot seed extract, may also be used and is derived from the seed of *Daucus carota sativa*.

A further expedient is the use of dexpanthenol (panthenol, pro-vitamin B5) which is part of the B complex and precursor of pantothenic acid (vitamin B5). Dexpanthenol is a nutritional and topical factor as a source of vitamin B5, which is present in all cells and is a constituent of co-enzyme A. The activated acetates from acetylation reactions (Krebs cycle) are essential in the synthesis or lipids and proteins and the linkages between these two and carbohydrates. Dexpanthenol is used in these preparations for it is a quick and deep penetrating moisturizer and promotes normal skin keratinization. It has been shown to stimulate fibroblast proliferation and also to promote tissue repair and wound healing.

In accordance with the present invention, as a further preferred embodiment, one or more cell growth stimulating compounds in suitable amounts effective for stimulating the growth of cells which encompass, or surround, and are injured or are responsible for skin repair and for healing of wounds from ultraviolet radiation damage will be incorporated in the present preparations of creams, lotions, gels, ointments, balms or sprays (aerosols).

Local anesthetics such as benzocaine and related caines may be added to ameliorate discomfort and pain, and tissue respiratory factor, which also diminishes discomfort and stimulates fibroblast's metabolic functions to deposit collagen. Also, to enhance the healing of skin, the patent application adds epidermal growth factor which stimulates epithelial cell growth, vital in the epidermis repair process, to accelerate wound healing.

I claim:

1. A method for enhancing repair from free radical damage to skin as a result of treatment of the skin with exfoliants, chemosurgery or laser therapy comprising topically applying active ingredients in a suitable topical carrier to skin damaged by exfoliants, chemosurgery or laser therapy, said active ingredients comprising glutathione and selenoamino acid in amounts suitable for enhancing repair of skin from free radical damage.

2. The method of claim 1 further comprising inclusion of acetyl-L-carnitine.

3. The method of claim 1 further comprising inclusion of melanin.

4. The method of claim 1 further comprising inclusion of superoxide dismutase.

5. The method of claim 1 further comprising inclusion of epidermal growth factor.

6. The method of claim 1 further comprising inclusion of fibroblast growth factor.

7. The method of claim 1 further comprising inclusion of glutathione reductase.

8. The method of claim 1 further comprising inclusion of L-cysteine.

9. The method of claim 1 further comprising inclusion of tissue respiratory factor.

10. The method of claim 1 further comprising inclusion of a zinc salt.

* * * * *